US011712411B2

(12) United States Patent
Zhou et al.

(10) Patent No.: US 11,712,411 B2
(45) Date of Patent: *Aug. 1, 2023

(54) LIP COMPOSITIONS CAPABLE OF FORMING A MULTILAYER STRUCTURE AFTER APPLICATION TO LIPS

(71) Applicant: L'OREAL, Paris (FR)

(72) Inventors: XianZhi Zhou, Millburn, NJ (US); Tsang-Min Huang, Scotch Plains, NJ (US); Jody Ebanks, Bloomfield, NJ (US); Mariko Hasebe, New York, NY (US); Hy Si Bui, Piscataway, NJ (US); Chunhua Li, Hillsborough, NJ (US); Rita Jaky El-Khouri, Clark, NJ (US); Rabia Ahmad, Clark, NJ (US)

(73) Assignee: L'OREAL, Paris (FR)

( * ) Notice: Subject to any disclaimer, the term of this patent is extended or adjusted under 35 U.S.C. 154(b) by 157 days.

This patent is subject to a terminal disclaimer.

(21) Appl. No.: 17/083,447

(22) Filed: Oct. 29, 2020

(65) Prior Publication Data

US 2021/0038495 A1 Feb. 11, 2021

Related U.S. Application Data

(63) Continuation-in-part of application No. 16/399,245, filed on Apr. 30, 2019, now abandoned, and a continuation-in-part of application No. 16/086,960, filed as application No. PCT/US2017/025370 on Mar. 31, 2017, now Pat. No. 11,464,731, which is a continuation-in-part of application No. 15/445,684, filed on Feb. 28, 2017, now abandoned, and a continuation-in-part of application No. 15/445,634, filed on Feb. 28, 2017, now Pat. No. 10,369,387, and a continuation-in-part of application No. 15/253,114, filed on Aug. 31, 2016, now Pat. No. 11,185,490, and a continuation-in-part of application No. 15/253,071, filed on Aug. 31, 2016, now Pat. No. 11,179,313, which is a continuation-in-part of application No. 15/144,622, filed on May 2, 2016, now Pat. No. 10,772,806, said application No. 15/253,114 is a continuation-in-part of application No. 15/144,716, filed on May 2, 2016, now Pat. No. 10,744,074, and a continuation-in-part of application No. 15/144,698, filed on May 2, 2016, now Pat. No. 10,675,226, said application No. 15/253,071 is a continuation-in-part of application No. 15/144,698, filed on May 2, 2016, now Pat. No. 10,675,226, said application No. 15/253,114 is a continuation-in-part of application No. 15/144,622, filed on May 2, 2016, now Pat. No. 10,772,806, said application No. 15/253,071 is a continuation-in-part of application No. 15/144,716, filed on May 2, 2016, now Pat. No. 10,744,074.

(60) Provisional application No. 62/316,309, filed on Mar. 31, 2016.

(51) Int. Cl.
*A61K 8/81* (2006.01)
*A61K 8/891* (2006.01)
*A61Q 1/04* (2006.01)

(52) U.S. Cl.
CPC ............ *A61K 8/8152* (2013.01); *A61K 8/891* (2013.01); *A61Q 1/04* (2013.01); *A61K 2800/31* (2013.01); *A61K 2800/54* (2013.01); *A61K 2800/594* (2013.01)

(58) Field of Classification Search
CPC .. A61K 8/8152; A61K 8/891; A61K 2800/31; A61K 2800/54; A61K 2800/594; A61Q 1/04
See application file for complete search history.

(56) References Cited

U.S. PATENT DOCUMENTS

| | | | |
|---|---|---|---|
| 4,767,741 A | 8/1988 | Komor et al. |
| 5,849,316 A | 12/1998 | Mullul et al. |
| 5,882,635 A | 3/1999 | Ramin et al. |
| 5,985,297 A | 11/1999 | Mullul et al. |
| 6,019,962 A | 2/2000 | Rabe et al. |
| 6,071,503 A | 6/2000 | Drechsler et al. |
| 6,340,466 B1 | 1/2002 | Drechsler et al. |
| 6,406,683 B1 | 6/2002 | Drechsler et al. |
| 6,482,398 B1 | 11/2002 | Rabe et al. |
| 6,620,417 B1 | 9/2003 | Jose et al. |
| 6,811,770 B2 | 11/2004 | Ferrari et al. |
| 7,785,574 B2 | 8/2010 | Bobka et al. |
| 7,988,981 B2 | 8/2011 | Di Puccio Pagano |
| 8,277,791 B2 | 10/2012 | Zheng et al. |

(Continued)

FOREIGN PATENT DOCUMENTS

KR 10-2007-0004885 A 1/2007
WO 2014095821 6/2014

(Continued)

OTHER PUBLICATIONS

Office Action dated May 19, 2022, in corresponding Korean Patent Application No. 10-2018-7031537 (with English Translation), 13 pages.

(Continued)

*Primary Examiner* — Blessing M Fubara
(74) *Attorney, Agent, or Firm* — Womble Bond Dickinson (US) LLP

(57) ABSTRACT

Lip compositions including at least one semi-crystalline acrylate copolymer, wherein the compositions include at least two components prior to mixing and application to lips and are capable of forming a multilayer structure after application to lips, are provided.

13 Claims, No Drawings

(56) References Cited

U.S. PATENT DOCUMENTS

| | | | |
|---|---|---|---|
| 8,318,187 B2 | 11/2012 | Sabino et al. | |
| 9,205,039 B2 | 12/2015 | Brown et al. | |
| 9,789,055 B2 | 10/2017 | Bui et al. | |
| 10,272,027 B2 | 4/2019 | Bui et al. | |
| 10,369,387 B2 * | 8/2019 | El-Khouri | A61K 8/893 |
| 10,426,722 B2 | 10/2019 | El-Khouri et al. | |
| 10,675,226 B2 * | 6/2020 | El-Khouri | A61K 8/03 |
| 10,744,074 B2 * | 8/2020 | El-Khouri | A61K 8/8158 |
| 10,772,806 B2 * | 9/2020 | El-Khouri | A61K 8/895 |
| 10,780,040 B2 * | 9/2020 | El-Khouri | A61K 8/895 |
| 10,881,601 B2 * | 1/2021 | Rosario-Melendez | A61K 8/91 |
| 10,894,010 B2 * | 1/2021 | El-Khouri | A61K 8/73 |
| 10,952,954 B2 * | 3/2021 | Rosario-Melendez | A61K 8/27 |
| 11,179,313 B2 * | 11/2021 | El-Khouri | A61K 8/31 |
| 11,185,490 B2 * | 11/2021 | El-Khouri | A61K 8/31 |
| 2001/0031268 A1 | 10/2001 | Baldwin et al. | |
| 2001/0031269 A1 | 10/2001 | Arnaud | |
| 2003/0068344 A1 | 4/2003 | Ferrari et al. | |
| 2004/0141933 A1 | 7/2004 | Luo et al. | |
| 2005/0089498 A1 | 4/2005 | Patil et al. | |
| 2005/0186166 A1 | 8/2005 | Patil et al. | |
| 2005/0201961 A1 | 9/2005 | Lu et al. | |
| 2005/0226832 A1 | 10/2005 | Bobka et al. | |
| 2005/0244355 A1 | 11/2005 | Sabino et al. | |
| 2005/0249758 A1 | 11/2005 | Di Puccio Pagano | |
| 2006/0292096 A1 | 12/2006 | Yu | |
| 2007/0093619 A1 | 4/2007 | Bui et al. | |
| 2007/0142521 A1 | 6/2007 | Brahms et al. | |
| 2008/0305056 A1 | 12/2008 | Jenni et al. | |
| 2008/0305068 A1 | 12/2008 | Zheng et al. | |
| 2011/0147259 A1 | 6/2011 | Binder et al. | |
| 2012/0128786 A1 | 5/2012 | Saffie-Siebert | |
| 2012/0276034 A1 | 11/2012 | Zheng et al. | |
| 2012/0308500 A1 | 12/2012 | Hart | |
| 2013/0164229 A1 | 6/2013 | Mendoza | |
| 2014/0154196 A1 | 6/2014 | Cavazzuti et al. | |
| 2014/0154199 A1 | 6/2014 | Dussaud et al. | |
| 2014/0170105 A1 | 6/2014 | Chen et al. | |
| 2015/0366779 A1 | 12/2015 | Bui et al. | |
| 2015/0366780 A1 | 12/2015 | Bui et al. | |
| 2015/0366782 A1 | 12/2015 | Bui et al. | |
| 2016/0228349 A1 | 8/2016 | Dussaud et al. | |
| 2017/0135946 A1 | 5/2017 | Novack et al. | |
| 2017/0281478 A1 | 10/2017 | El-Khouri | |
| 2017/0281518 A1 | 10/2017 | El-Khouri | |
| 2017/0281519 A1 | 10/2017 | El-Khouri | |
| 2017/0281520 A1 | 10/2017 | El-Khouri | |
| 2017/0281521 A1 | 10/2017 | El-Khouri | |
| 2019/0099359 A1 | 4/2019 | Rosario-Melendez et al. | |

FOREIGN PATENT DOCUMENTS

| | | |
|---|---|---|
| WO | 2015193413 A1 | 12/2015 |
| WO | 2017173267 | 3/2017 |
| WO | 2017173270 | 3/2017 |

OTHER PUBLICATIONS

Sagitani, "Making Homogeneous and Fine Droplet O/W Emulsions Using Nonionic Surfactants", JAOCS, pp. 738-743, 1981.

Office Action dated Sep. 16, 2021 in corresponding Korean Patent Application No. 10-2018-7031537 (with English Translation), 19 pages.

"Xiameter® PMX-200 Silicone Fluid 30,000 CS," Xiameter® Material Safety Data Sheet, Version 3.0, published Sep. 13, 2017, p. 1-12.

"Xiameter® PMX-200 Silicone Fluid, 5,000-60,000 cst," Xiameter® from Dow Corning, published Feb. 18, 2015, p. 1-3.

"Mega Last Liquid Lipstick Liquid Lipstick: Improved Color Intensity, Non-transfer," Formulation 01451, Dow Corning, Formulation Information Color Cosmetics ©, 2010 Dow Corning Corporation, p. 1-2.

Alex C.M. Kuo, "Poly(dimethylsiloxane)," Polymer Data Handbook ©, 1999 by Oxford University Press, Inc., p. 1-25.

International Search Report and Written Opinion dated Jul. 11, 2017 in PCT/US 2017/025376.

"Triethoxy Caprylylsilane Treatment-11S," Kobo Products Inc., published Jul. 14, 2017.

"Introduction to Silicone Fluids," Clearco Products Co., Inc.,p. 1-4, Aug. 7, 2006.

* cited by examiner

LIP COMPOSITIONS CAPABLE OF FORMING A MULTILAYER STRUCTURE AFTER APPLICATION TO LIPS

FIELD OF THE INVENTION

The present invention relates to lip compositions capable of forming a multilayer structure after application to lips. Such compositions allow for benefits associated with multilayer lip products without having to engage in a multi-step application process.

DISCUSSION OF THE BACKGROUND

Lip compositions, in particular lip gloss compositions, are typically formulated to possess shine or gloss characteristics upon application. Although such compositions may purport to be long-wearing, unfortunately, such compositions do not possess good transfer-resistance properties and application properties (for example, slip) as well as good appearance properties (for example, shine, gloss or matte properties).

Thus, there remains a need for improved "single step" lip compositions having improved cosmetic properties, particularly good wear, transfer-resistance, slip, shine, gloss and/or matte characteristics upon application.

Accordingly, one aspect of the present invention is a care and/or makeup and/or treatment composition for lips which has good cosmetic properties such as, for example, good adhesion, transfer-resistance, slip, gloss (or shine), and/or matte upon application, and which can be applied to lips without having to engage in a multi-step application process.

SUMMARY OF THE INVENTION

The present invention relates to lip compositions, in particular lip gloss compositions, comprising at least one semi-crystalline acrylate copolymer, wherein the compositions comprise at least two components prior to mixing and application to lips and wherein the compositions are capable of forming a multilayer structure after application to lips.

The present invention also relates to anhydrous lip compositions, in particular lip gloss compositions, comprising at least one semi-crystalline acrylate copolymer, wherein the compositions comprise at least two components prior to mixing and application to lips and wherein the compositions are capable of forming a multilayer structure after application to lips.

The present invention also relates to lip compositions, in particular lip gloss compositions, in the form of a dispersion comprising at least one semi-crystalline acrylate copolymer, wherein the compositions comprise at least two components prior to mixing and application to lips and wherein the compositions are capable of forming a multilayer structure after application to lips. The dispersions may contain water, or the dispersion may be anhydrous.

The present invention also relates to methods of treating, caring for and/or making up lips by applying compositions of the present invention to lips in an amount sufficient to treat, care for and/or make up lips.

The present invention also relates to methods of enhancing the appearance of lips by applying compositions of the present invention to lips in an amount sufficient to enhance the appearance of lips.

The present invention also relates to methods of applying compositions of the present invention to lips comprising mixing or blending the composition so that the components are temporarily substantially homogeneous, and applying the composition comprising the temporarily substantially homogeneous components to lips. Subsequent to application to lips, the components become non-homogeneous to form a multilayer structure on lips.

The present invention also relates to kits comprising (1) at least one container; (2) at least one applicator; and (3) at least one lip composition, in particular at least one lip gloss composition, comprising at least one semi-crystalline acrylate copolymer, wherein the compositions comprise at least two components prior to mixing and application to lips and wherein the compositions are capable of forming a multilayer structure after application to lips.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied.

"Polymer" as used herein means a compound which is made up of at least two monomers.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, hydroxyalkyl groups, and polysiloxane groups. The substituent(s) may be further substituted.

"Volatile", as used herein, means having a flash point of less than about 100° C.

"Non-volatile", as used herein, means having a flash point of greater than about 100° C.

"Anhydrous" means the compositions contain less than 1% water. Preferably, the compositions of the present invention contain less than 0.5% water, and most preferably no water.

"Transfer resistance" as used herein refers to the quality exhibited by compositions that are not readily removed by contact with another material, such as, for example, a glass, lips, skin or artificial skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as lips followed by kissing another material, for example, a glass, lips, skin or artificial skin, against the lips after expiration of a certain amount of time following application, such as 15 minutes after application. The amount of composition transferred to the substrate may then be evaluated and compared. For example, a composition may be transfer resistant if a majority of the product is left on the wearer's lips. Further, the amount transferred may be compared with that transferred by other compositions, such as commercially available compositions. In a preferred embodiment of the present invention, little or no composition is transferred to the substrate from the lips.

"Gloss" in compositions as used herein refers to compositions having with an average gloss, measured at 60°, of greater than or equal to 35, for example 40, preferably 45, 55, 60 or 65 out of 100, including all ranges and subranges there between such as 35-65, 40-65, etc.

The term "average gloss" denotes the gloss as it can be measured using a gloss meter, for example by spreading a layer of the composition to be tested, between 50 µm and 500 µm in thickness, on a Leneta contrast card or BYK Opacity chart of reference Form 1A Penopac using an automatic spreader. The layer covers at least the white and/or black background of the card. The deposit is left to dry for 24 hours at a temperature of room temperature and then the gloss is measured at 60° on the white background using a Byk Gardner gloss meter of reference microTRI-GLOSS. This measurement (of between 0 and 100) is repeated at least three times, and the average gloss is the average of the at least three measurements carried out.

The composition of the present invention may be in any form, either liquid or non-liquid (semi-solid, soft solid, solid, etc.). For example, it may be a paste, a solid, a gel, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel. The composition of the invention may, for example, comprise an external or continuous fatty phase. The composition can also be a molded composition or cast as a stick or a dish.

The compositions and methods of the present invention can comprise, consist of, or consist essentially of the essential elements and limitations of the invention described herein, as well as any additional or optional ingredients, components, or limitations described herein or otherwise useful in personal care.

Lip Compositions Capable of Forming a Multilayer Structure

In accordance with the present invention, lip compositions, in particular lip gloss compositions, capable of forming a multilayer structure after application to lips are provided. Such compositions allow for benefits associated with multilayer lip products without having to engage in a multi-step application process.

According to preferred embodiments, the lip compositions of the present invention possess low temperature stability in which the compositions, when cooled to a temperature of approximately 4 degrees Celsius and kept at this temperature for at least 1 month, preferably for at least 2 months, do not solidify (in some cases, 2 months).

In accordance with the present invention, the lip compositions, in particular lip gloss compositions, of the present invention comprise at least two Components, hereinafter referred to as "Component A" and "Component B."

Component A is the component of the compositions of the present invention which forms the layer of the multilayer structure which is closest to the lip after application of the composition to the lip. This layer of the multilayer structure is hereinafter referred to as "Layer A." In accordance with preferred embodiments, Component A/Layer A has an affinity for the surface of the lip owing to the surface energy characteristics between the two.

Component B is the component of the compositions of the present invention which forms the layer of the multilayer structure which is farthest away from the lip after application of the composition to the lip. This layer of the multilayer structure is hereinafter referred to as "Layer B." In accordance with preferred embodiments, Component B/Layer B has an affinity for the air interface.

In accordance with the present invention, all weight amounts and ratios set forth herein referring to Component A and Component B refer to amounts of active material (that is, non-volatile material) in these components. Similarly, all weight amounts and ratios set forth herein referring to Layer A and Layer B refer to amounts of active material as Layer A and Layer B are present after evaporation of volatile solvent.

Prior to application to a lip, Component A and Component B are non-homogeneous in the compositions of the present invention. That is, Component A and Component B are of non-uniform droplet sizes which may change over time (in contrast to an emulsion which possesses uniform droplet sizes stable over time) or Component A and Component B form visibly separate layers in the compositions of the present invention when the compositions are at rest. Preferably, non-homogeneity of the non-homogeneous components results from an incompatibility between the two components when the composition is at rest, incompatibility between the two components after application to lips, or both.

Preferably, non-homogeneity of the non-homogeneous components results from differences such as, for example, differences in viscosity, glass transition temperature, interfacial tension, solubility parameters, density, and/or chemical/structural incompatibility of the components, and/or differences induced by temperature and/or pressure.

For example, non-homogeneity of the non-homogeneous components when the composition is at rest can result from, for example, chemical/structural incompatibility, differences in the interfacial tension between the components such as, for example, differences in the interfacial tension between the phases within mutually compatible solvent(s), differences in viscosity, differences in the glass transition temperatures of the polymers within each phase and/or differences induced by temperature and/or pressure.

For example, non-homogeneity of the non-homogeneous components when the composition is being applied can result from, for example, chemical/structural incompatibility, differences in the interfacial tension between the components, differences in density of the components after solvent evaporation, and/or differences induced by temperature and/or pressure.

Immediately prior to application and/or during application to a lip, the composition of the present invention is mixed or blended such that Component A and Component B are temporarily substantially homogeneous upon application of the composition of the present invention to lips. By "substantially homogeneous," it is meant that the composition appears to be homogeneous to the naked eye but does not contain uniform droplet size when observed under a microscope. By "temporarily substantially homogeneous," it is meant that the composition is unstable and its appearance will not remain substantially homogeneous—the composition will revert back non-homogeneity (when viewed with the naked eye). That is, after the composition is allowed to rest for a period of time after mixing or blending such as, for example, 1 hour, 12 hours, 24 hours or 72 hours, Components A and B revert back to non-homogeneity Accordingly, compositions of the present invention have properties such that, prior to mixing or blending, Component A and Component B are non-homogeneous; immediately after mixing or blending the composition, Component A and Component B are temporarily substantially homogeneous; and after allowing the composition to rest at room temperature for a period of time after mixing or blending such as 1 hour, 12 hours, 24 hours or 72 hours, Component A and Component B return to non-homogeneity.

After the composition of the present invention has been applied to a lip, Component A separates from Component B. As the composition dries on the lip to which it has been applied, Component A and Component B form a multilayer structure comprising Layer A and Layer B, respectively, on the lip such as, for example:

| LAYER B |
| LAYER A |
| LIP |

According to preferred embodiments of the present invention, after compositions of the present invention have been applied to a lip, Component B results in Layer B which is level: that is, Layer B is planar such that it has refractive properties to impart shine or gloss to the composition. In accordance with these embodiments, Component B has self-leveling properties: it results in a level Layer B after application. The gloss or shine of such compositions can be enhanced, if desired, by addition of one or more shine or gloss enhancing agents having high refractive index properties. Alternatively, such compositions can be provided with matte properties by addition of one or more mattifying agents.

According to preferred embodiments of the present invention, after compositions of the present invention have been applied to a lip, Component B results in Layer B which is not-level: that is, Layer B is not planar such that it imparts matte properties to the composition. In accordance with these embodiments, Component B does not have self-leveling properties: it results in a non-level Layer B after application. The matte properties of such compositions can be enhanced, if desired, by addition of one or more mattifying agents. Alternatively, such compositions can be provided with shine or gloss properties by addition of one or more shine or gloss enhancing agents having high refractive index properties.

In accordance with the present invention, the multilayer structure comprises Layer A and Layer B. In certain instances, depending on factors such as ingredient ratios, ingredient concentrations, solvent evaporation characteristics, and Tg of polymers, the layers might be intermixed slightly with each other after application to a lip, resulting in Layer A having a larger amount of A and a smaller amount of B greater and/or Layer B having a larger amount of B and a smaller amount of A. Preferably, Layer A comprises 40% or less of Layer B, preferably 30% or less of Layer B, preferably 20% or less of Layer B, preferably 10% or less of Layer B, and preferably 5% or less of Layer B, including all ranges and subranges therebetween. Similarly, preferably, Layer B comprises 40% or less of Layer A, preferably 30% or less of Layer A, preferably 20% or less of Layer A, preferably 10% or less of Layer B, and preferably 5% or less of Layer A, including all ranges and subranges therebetween.

Factors affecting the separation of Component A and Component B after application to a lip can include, for example, those properties discussed above including but not limited to the surface energy of the substrate, the density of each Component, the evaporation properties of the solvent (s), the Tg of the film formers, and/or the viscosity of the film formers.

Although not wishing to be bound by any particular theory, it is believed that Component A should have surface energy properties closer to the surface energy properties of the lip to which it is applied than Component B. For example, the surface energy of skin is estimated to be 36 mN/m. Accordingly, where Component A has a surface energy of about 36 mN/m, it is believed that Component A should migrate to the skin. Component B would preferably have a lower surface energy, making it more likely that it would migrate toward the air interface.

Although not wishing to be bound by any particular theory, it is believed that interfacial tension of Components A and B affects separation (in particular, the rate at which the Components A and B separate after application). It is believed that such separation can be affected by differences such as those discussed above such as, for example, differences in temperature of the Components A and B, in the Tg of the Components A and B (the higher the Tg of a component, the longer it will take for separation), in the weight fraction of the film formers, and/or in the pressure of the Components A and B.

Such differences will also be discussed further below.

Glass Transition Temperature (Tg)

According to preferred embodiments, Component A and/or Component B comprises at least one film forming agent having at least one glass transition temperature lower than 60° C., preferably lower than 55° C., preferably lower than 50° C., and preferably lower than normal human body temperature (98.6° F. or 37° C.). Preferably, Component A and/or Component B comprises at least one film forming agent which has all of its glass transition temperature(s) below human body temperature (98.6° F. or 37° C.). A plasticizer can be added to adjust Tg of the film forming agent(s) as is known in the art. According to preferred embodiments, Layer A and Layer B both comprise at least one forming agent having a glass transition temperature of less than 37° C.

A preferred method of determining Tg is to remove all volatile solvent from the Layer, and determining Tg by Differential Scanning calorimetry.

Density

According to preferred embodiments, Component A and Component B have different density properties, and the difference is such that Component A and Component B are non-homogeneous in the compositions of the present invention. Preferably, Component A/Layer A and Component B/Layer B have a density difference of 0.001-1 kg/m$^3$, preferably 0.005-0.8 kg/m$^3$, and preferably 0.01-0.6 kg/m$^3$.

Temperature

According to preferred embodiments, Component A and Component B are affected by temperature, and the effect is such that Component A and Component B are non-homogeneous in the compositions of the present invention at temperatures below 50° C. for a predetermined amount of time as is known in the art unlike emulsions which are considered to be stable under such conditions.

Weight Fraction

According to preferred embodiments, Component A and/or Component B comprises at least one polymer such as, for example a film forming agent having a critical molecular weight of entanglement ($M_c$) such that:

If present in Component A, the at least one polymer has an $M_c<wMw$, where w=weight fraction and Mw=molecular weight of the polymer; and If present in Component B, the at least one polymer has $M_c \leq wMw \leq 10^8$ g/mol.

Further, according to preferred embodiments, the viscosity of the at least one polymer in Component B is greater than 350 cSt, preferably greater than 500 cSt, preferably greater than 750 cSt, and preferably greater than 1000 cSt, including all ranges and subranges therebetween.

Ingredients

Semi-Crystalline Acrylate Copolymer

According to the present invention, lip compositions, in particular lip gloss compositions, comprising at least one semi-crystalline acrylate copolymer, wherein the compositions comprise at least two components prior to mixing and application to lips and wherein the compositions are capable of forming a multilayer structure after application to lips, are provided.

A semi-crystalline acrylate copolymer is a compound that is solid at ambient temperature (25° C.) and changes from the solid to the liquid state reversibly, having at least one melting temperature less than about 35° C., preferably between about 25° C. to about 35° C., a hardness of more than 0.5 MPa at ambient temperature, and an anisotropic crystalline organization in the solid state.

The semi-crystalline acrylate copolymer(s) according to the invention preferably contain(s) crystallizable side chains, which are homopolymers or copolymers. The semi-crystalline acrylate copolymers of the invention containing crystallizable blocks are block or multiblock copolymers. They may be obtained by polymerizing monomers containing reactive (or ethylenic) double bonds. When the polymers of the invention are polymers containing crystallizable side chains, these side chains are advantageously in random or statistical form.

The semi-crystalline acrylate copolymers useful in the invention may be made in particular from the polymerization, especially the free radical polymerization, of one or more ethylenically unsaturated monomers namely a vinyl, (meth)acrylic or allylic group. The term "(meth)acryl" and variations thereof, as used herein, means acryl or methacryl.

In general, the crystallizable units (chains or blocks) of semi-crystalline acrylate polymers according to the invention are derived from monomer(s) containing crystallizable block(s) or chain(s), used for manufacturing semi-crystalline polymers. These polymers are selected especially from homopolymers and copolymers resulting from the polymerization of at least one monomer containing crystallizable chain(s) that may be represented by formula:

where M represents an atom of the polymer skeleton;
X represents a spacer, can be a divalent group selected from

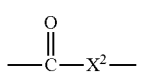

where $X^2$ is O, S or NH, and/or a group $(CH_2)_n$ or $(CH_2CH_2O)_n$ or $(CH_2O)$, which is linear or branched or cyclic, with n being an integer ranging from 0 to 22; and C representing a crystallizable group, can be hydrocarbon based aliphatic chains, they comprise hydrocarbon-based alkyl chains containing at least 11 carbon atoms and not more than 40 carbon atoms and better still not more than 24 carbon atoms. They are especially aliphatic chains or alkyl chains containing at least 12 carbon atoms, and they are preferably C14-C24, preferably C16-C22 alkyl chains.

As examples of monomers containing crystallizable chain(s): alkyl (meth)acrylates with the alkyl group being C14-C24, N-alkyl(meth)acryl-amides with the alkyl group being C14 to C24, vinyl esters containing alkyl with the alkyl group being C14 to C24, vinyl ethers containing alkyl or with the alkyl group being C14 to C24, and mixtures thereof.

The (meth)acrylic monomers may be chosen from, for example, acrylic acid, methacrylic acid, citraconic acid, itaconic acid, maleic acid, fumaric acid, crotonic acid, and maleic anhydride. Additional non-limiting examples of (meth)acrylic monomers include C1-C8 alkyl (meth)acrylic, such as, for example, methyl (meth)acrylic, ethyl (meth) acrylic, propyl (meth)acrylic, isopropyl (meth)acrylic, butyl (meth)acrylic, tert-butyl (meth)acrylic, pentyl(meth) acrylic, isopentyl (meth)acrylic, neopentyl (meth)acrylic, hexyl (meth)acrylic, isohexyl (meth)acrylic, 2-ethylhexyl (meth) acrylic, cyclohexyl (meth)acrylic, isohexyl (meth)acrylic, heptyl (meth)acrylic, isoheptyl (meth)acrylic, octyl (meth) acrylic, isooctyl (meth)acrylic, as well as combinations of any of the above.

The esters of (meth)acrylic monomers may be, by way of non-limiting example, C1-C8 alkyl (meth)acrylates such as methyl (meth)acrylate, ethyl (meth)acrylate, propyl (meth) acrylate, isopropyl (meth)acrylate, butyl (meth)acrylate, tert-butyl (meth)acrylate, pentyl(meth) acrylate, isopentyl (meth)acrylate, neopentyl (meth)acrylate, hexyl (meth)acrylate, isohexyl (meth)acrylate, 2-ethylhexyl (meth)acrylate, cyclohexyl (meth)acrylate, isohexyl (meth)acrylate, heptyl (meth)acrylate, isoheptyl (meth)acrylate, octyl (meth)acrylate, isooctyl (meth)acrylate, allyl (meth)acrylate, and combinations thereof. Additional and non-limiting examples include C1-C8 alkoxy (meth)acrylates, such as methoxy (meth)acrylate, ethoxy (meth)acrylate, propyl oxide (meth) acrylate, isopropyl oxide (meth)acrylate, butyl oxide (meth) acrylate, tert-butyl oxide (meth)acrylate, pentyl oxide (meth) acrylate, isopentyl oxide (meth)acrylate, neopentyl oxide (meth)acrylate. The esters may be, by way of non-limiting example, C2-C6 hydroxy alkyl (meth)acrylates, such as hydroxy ethyl (meth)acrylate, 2-hydroxypropyl (meth)acrylate, glycidyl (meth)acrylate, ethylene glycol di(meth)acrylate, polyethylene glycol mono(meth)acrylate, 1,4-butane diol di(meth)acrylate, 1,6,hexane diol di(meth) acrylate, and any combination thereof. The esters may be, by way of non-limiting example, aryl (meth)acrylates such as benzyl (meth)acrylate, phenyl (meth)acrylate, and any combination thereof. The esters can further contain amino groups such as aminoethyl (meth)acrylate, N,N-dimethylaminoethyl (meth)acrylate, N,N-dimethylaminopropyl (meth)acrylate, N,N-dimethylaminodimethylpropyl (meth) acrylate, N,N-diethyleaminoethyl (meth)acrylate, and N,N, N-trimethylaminoethyl (meth)acrylate; and salts of the ethylenic amines.

According to at least certain exemplary embodiments, the alkyl group of the esters may be either fluorinated or perfluorinated, e.g. some or all of the hydrogen atoms of the alkyl group are substituted with fluorine atoms. The monomers can also be silicone-containing monomers, such as, by way of non-limiting example, trifluoroethyl methacrylate, 2,2,3,3-tetrafluoropropyl methacrylate, 2,2,3,3,4,4-hexafluorobutyl methacrylate, perfluorooctyl methacrylate and perfluorooctyl acrylate; and silicone macromonomers.

The amides of (meth)acrylic monomers can, for example, be made of (meth)acrylamides, and especially N-alkyl (meth)acrylamides, in particular N—(C1-C12) alkyl (meth) acrylates such as N-ethyl (meth)acrylamide, N-t-butyl (meth)acrylamide, N-t-octyl (meth)acrylamide, N-methylol (meth)acrylamide and N-diacetone (meth)acrylamide, and any combination thereof.

The vinyl monomers can include, but are not limited to, vinyl cyanide compounds such as acrylonitrile and methacrylonitrile; vinyl esters such as vinyl formate, vinyl acetate, vinyl propionate, vinyl neodecanoate, vinyl pivalate, vinyl benzoate and vinyl t-butyl benzoate, triallyl cyanurate; vinyl halides such as vinyl chloride and vinylidene chloride; aromatic mono- or divinyl compounds such as styrene, □-methylstyrene, chlorostyrene, alkylstyrene, divinylbenzene and diallyl phthalate, and combination thereof. Other non-limiting ionic monomers can include para-styrensulfonic, vinylsulfonic, 2-(meth)acryloyloxyethylsulfonic, 2-(meth)acrylamido-2-methylpropylsulfonic acids.

The list of monomers given is not limiting, and it should be understood that it is possible to use any monomer known to those skilled in the art which includes acrylic and/or vinyl monomers (including monomers modified with a silicone chain).

By way of example, suitable polymers are described in document U.S. Pat. No. 5,519,063 or EP-A-0 550 745, the entire contents of both of which are hereby incorporated by reference. Suitable examples of semi-crystalline alkyl(meth) acrylates also include, but are not limited to, the Intelimer® or Doresco® products from the company Landec, such as those described in the brochure "Intelimer® Polymers" and/or are disclosed in U.S. patent application publication nos. 2006/0292095 and 2006/0263438, the disclosure of both of which is hereby incorporated by reference in their entirety; In accordance with the present invention, it is also possible to use acrylates/dimethicone copolymers such as those commercially available from Shin-Etsu, for example, the products sold under the tradenames, KP-561 (acrylates/stearyl acrylate/dimethicone acrylates copolymer), KP-562 (acrylates/behenyl acrylate/dimethicone acrylates copolymer), and mixtures thereof.

According to preferred embodiments, the semi-crystalline acrylate copolymer(s) is/are present in the compositions of the present invention in an amount ranging from greater than 1% to about 20% by weight relative to the total weight of the composition, for example from about 1 to about 15%, and for example from about 1 to 10%, including all ranges and subranges therebetween.

Silicone Wax Component

According to preferred embodiments of the present invention, lip compositions, in particular lip gloss compositions, further comprising a silicone wax component are provided.

A silicone "wax" is a compound that is solid at ambient temperature (25° C.) and changes from the solid to the liquid state reversibly, having a melting temperature of more than 25° C. and, for example, more than 30° C., which can be as high as 150° C., a hardness of more than 0.5 MPa at ambient temperature According to preferred embodiments of the present invention, the silicone wax component has a melting point of less than about 35° C., preferably a melting point of about 25° C. to about 35° C.

According to preferred embodiments, the silicone wax component comprises at least one C12-C22 dimethicone, and preferably at least one C16-C18 dimethicone.

According to preferred embodiments, the silicone wax component is present in the compositions of the present invention in an amount ranging from greater than 1% to about 20% by weight relative to the total weight of the composition, for example from about 1% to about 15%, and for example from about 1% to 10%, including all ranges and subranges therebetween.

According to preferred embodiments of the present invention, the weight ratio of semi-crystalline acrylate copolymer to silicone wax in the compositions of the present invention ranges from about 10:1 to about 1:10, preferably from about 5:1 to about 1:5, and preferably from about 4:1 to about 1:4, including all ranges and subranges therebetween Other Ingredients Component A and Component B can differ in various ways based primarily on the different functionalities associated with Layer A and Layer B. For example, where Layer A performs a transfer-resistance or adherence function, ingredients of Component A can be chosen to effect transfer-resistance or adherence. Similarly, where Layer A performs a color-enhancing function, at least one coloring agent can be added to Component A. And, for example, where Layer B performs a gloss- or shine-enhancing function and/or and provides a better feel (for example, affords a more comfortable feeling) and/or provides a barrier layer to inhibit color transfer, ingredients of Component B can be chosen to effect gloss, shine, comfort and/or barrier layer properties. However, it should be understood that at the interface of Layer A and Layer B, the interface of Layer A may possess properties more associated with Layer B (for example, shine) while Layer B may possess properties more associated with Layer A (for example, adhesion).

According to preferred embodiments, Component A comprises at least one film forming agent, at least one coloring agent, or both, and Layer A provides adhesion, transfer-resistance and/or color properties to the multilayer structure. According to such embodiments, Component B may comprise at least one shine-enhancing agent, at least one comfort agent and/or at least one barrier agent, and Layer B provides shine, comfort and/or barrier properties to the multilayer structure.

According to preferred embodiments, the compositions of the present invention contain less than 1% fluorinated compound.

According to preferred embodiments, the compositions of the present invention contain less than 0.5% fluorinated compound.

According to preferred embodiments, the compositions of the present invention contain no fluorinated compound.

According to preferred embodiments, at least one of the same solvent(s) is used in Component A and Component B. Preferably, of total solvent present in each Component, the majority in each Component is the same.

According to preferred embodiments, the weight ratio of Component A to Component B is from 1:75 to 20:1, preferably from 1:50 to 10:1, and preferably from 1:20 to 10:1, including all ranges and subranges therebetween.

Examples of acceptable ingredients added to Component A and/or Component B are discussed below.

Film Forming Agent (Film Former)

According to preferred embodiments, Component A comprises at least one film forming agent having at least one glass transition temperature which is lower than normal human body temperature (98.6° F.). Preferably, the at least one film forming agent has all of its glass transition temperature(s) below normal human body temperature (98.6° F.). The Tg property of the at least one film forming agent can result from various ways known in the art such as, for example, the Tg of the film forming agent itself, the combination of different film forming agents to achieve a Tg lower than normal human body temperature, or the combination of film forming agent(s) and plasticizer(s) to achieve a Tg lower than normal human body temperature.

Examples of acceptable classes of film forming agents include acrylic polymers, silicone resins, silicone acrylate copolymers, vinyl pyrrolidone (VP) containing homopolymers and copolymers, polyurethanes, polyolefins and mixtures thereof.

Preferably, the film forming agent(s) is/are selected from the group consisting of silicone resins, silicone acrylate copolymers, acrylate copolymers and mixtures thereof.

Silicone Resin Film Former

As used herein, the term "resin" means a crosslinked or non-crosslinked three-dimensional structure. Silicone resin nomenclature is known in the art as "MDTQ" nomenclature, whereby a silicone resin is described according to the various monomeric siloxane units which make up the polymer.

Each letter of "MDTQ" denotes a different type of unit. The letter M denotes the monofunctional unit $(CH_3)_3SiO_{1/2}$. This unit is considered to be monofunctional because the silicone atom only shares on oxygen when the unit is part of a polymer. The "M" unit can be represented by the following structure:

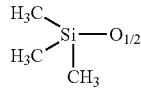

At least one of the methyl groups of the M unit may be replaced by another group, e.g., to give a unit with formula $[R(CH_3)_2]SiO_{1/2}$, as represented in the following structure:

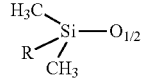

wherein R is chosen from groups other than methyl groups. Non-limiting examples of such groups other than methyl groups include alkyl groups other than methyl groups, alkene groups, alkyne groups, hydroxyl groups, thiol groups, ester groups, acid groups, ether groups, wherein the groups other than methyl groups may be further substituted.

The symbol D denotes the difunctional unit $(CH_3)_2SiO_{2/2}$ wherein two oxygen atoms bonded to the silicone atom are used for binding to the rest of the polymer. The "D" unit, which is the major building block of dimethicone oils, can be represented as:

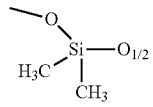

At least one of the methyl groups of the D unit may be replaced by another group, e.g., to give a unit with formula $[R(CH_3)_2]SiO_{1/2}$.

The symbol T denotes the trifunctional unit, $(CH_3)SiO_{3/2}$ and can be represented as:

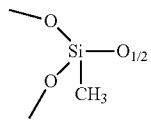

At least one of the methyl groups of the T unit may be replaced by another group, e.g., to give a unit with formula $[R(CH_3)_2]SiO_{1/2}$.

Finally, the letter Q means a tetrafunctional unit $SiO_{4/2}$ in which the silicon atom is bonded to four hydrogen atoms, which are themselves bonded to the rest of the polymer.

Thus, a vast number of different silicone polymers can be manufactured. Further, it would be clear to one skilled in the art that the properties of each of the potential silicone polymers will vary depending on the type(s) of monomer(s), the type(s) of substitution(s), the size of the polymeric chain, the degree of cross linking, and size of any side chain(s).

Non-limiting examples of silicone polymers include siloxysilicates and silsesquioxanes.

A non-limiting example of a siloxysilicate is trimethylsiloxysilicate, which may be represented by the following formula:

$[(CH_3)_3XSiXO]_xX(SiO_{4/2})_y$ (i.e, MQ units) wherein x and y may, for example, range from 50 to 80. Silsesquioxanes, on the other hand, may be represented by the following formula:

$(CH_3SiO_{3/2})_x$ (i.e., T Units) wherein x may, for example, have a value of up to several thousand.

Resin MQ, which is available from Wacker, General Electric and Dow Corning, is an example of an acceptable commercially-available siloxysilicate. For example, trimethylsiloxysilicate (TMS) is commercially available from General Electric under the tradename SR1000 and from Wacker under the tradename TMS 803. TMS is also commercially available from Dow Chemical in a solvent, such as for example, cyclomethicone. However, according to the present invention, TMS may be used in the form of 100% active material, that is, not in a solvent.

Suitable silicon resins comprising at least one T unit in accordance with the present invention are disclosed, for example, in U.S. patent applications 2007/0166271, 2011/0038820, 2011/0002869, and 2009/0214458, the entire contents of which are hereby incorporated by reference in their entirety.

Where the silicone resin contains at least one T unit, it may thus be, for example, a T, MT, MTQ or MDTQ resin.

According to preferred embodiments, the unit composition of the silicone resin can be at least 50% T units, or at least 70% T units, or at least 80% T units, or at least 90% T units.

In the M, D and T units listed as examples above, at least one of the methyl groups may be substituted. According to preferred embodiments, the at least one silicone resin comprising at least one trifunctional unit of formula $(R)SiO_{3/2}$ is chosen from the silsesquioxanes of formula: $((R')SiO_{3/2})_x$, in which x ranges from 100 to 500 and R' is chosen, independently by trifunctional unit, from a hydrocarbon-based group containing from 1 to 10 carbon atoms or a hydroxyl group, on the condition that at least one R' is a hydrocarbon-based group. According to preferred embodiments, the hydrocarbon-based group containing from 1 to 10 carbon atoms is a methyl group. According to preferred embodiments, the at least one silicone resin comprising at least one trifunctional unit of formula $(R)SiO_{3/2}$ is chosen from the silsesquioxanes of the formula: $((R')SiO_{3/2})_x$, in which x ranges from 100 to 500 and R' is chosen, independently by unit, from $CH_3$, a hydrocarbon-based group containing from 2 to 10 carbon atoms, or a hydroxyl group, on the condition that at least one R' is a hydrocarbon-based group.

According to preferred embodiments, the T resins may contain M, D and Q units such that at least 80 mol % or at least 90 mol %, relative to the total amount of silicones, are T units. The T resins may also contain hydroxyl and/or alkoxy groups. The T resins may have a total weight of hydroxyl functions ranging from 2% to 10% and a total weight of alkoxy functions that may be up to 20%; in some embodiments, the total weight of hydroxyl functions ranges from 4% to 8% and the total weight of alkoxy functions may be up to 10%.

The silicone resin may be chosen from silsesquioxanes that are represented by the following formula: $((CH_3)SiO_{3/2})_x$, in which x may be up to several thousand and the $CH_3$ group may be replaced with an R group, as described previously in the definition of the T units. The number x of T units of the silsesquioxane may be less than or equal to 500, or it may range from 50 to 500, including all ranges and subranges therebetween. The molecular weight of the silicone resin may range from 500 to 50,000 g/mol, from 500 to 20,000 g/mol, or from 500 to 10,000 g/mol, including all ranges and subranges therebetween.

As suitable examples of these silicone resins containing at least one T unit, mention may be made of:

polysilsesquioxanes of formula $((R)SiO_{3/2})_x$ (T units) in which x is greater than 100, in which the R groups may independently be methyl or other substituents as defined above;

polymethylsilsesquioxanes, which are polysilsesquioxanes in which R is a methyl group. Such polymethylsilsesquioxanes are described, for example, in U.S. Pat. No. 5,246,694, the entire contents of which is hereby incorporated by reference in its entirety;

polypropylsilsesquioxanes, in which R is a propyl group. These compounds and their synthesis are described, for example, in patent application WO 2005/075567, the entire contents of which is hereby incorporated by reference in its entirety; and polyphenylsilsesquioxanes, in which R is a phenyl group. These compounds and their synthesis are described, for example, in patent application US 2004/0180011, the entire contents of which is hereby incorporated by reference in its entirety.

Examples of commercially available polymethylsilsesquioxane resins that may be mentioned include those sold:

by the company Wacker under the reference Resin MK such as Belsil PMS MK: polymer comprising $CH_3SiO_{3/2}$ repeating units (T units), which may also comprise up to 1% by weight of $(CH_3)_2SiO_{2/2}$ units (D units) and having an average molecular weight of about 10 000 g/mol. It is thought that the polymer is in a "cage" and "ladder" configuration as represented in the figures below. The average molecular weight of the units in "cage" configuration has been calculated as 536 g/mol. The majority of the polymer is in the "ladder" configuration with ethoxy groups at the ends. These ethoxy groups represent 4.5% by mass of the polymer. As these end groups can react with water, a small and variable amount of SiOH groups may also be present; and by the company Shin-Etsu under the references KR-220L, which are composed of T units of formula $CH_3SiO_{3/2}$ and have Si—OH (silanol) end groups, under the reference KR-242A, which comprise 98% of T units and 2% of dimethyl D units and have Si—OH end groups or alternatively under the reference KR-251 comprising 88% of T units and 12% of dimethyl D units and have Si—OH end groups.

Examples of commercially available polypropylsilsesquioxane resins that may be mentioned include those sold:

by the company Dow Corning under the reference Dow Corning 670 Fluid or 680 Fluid. Typically such commercially available products are polypropylsilsesquioxane diluted in volatile oil such as volatile hydrocarbon oil or volatile silicone oil such as D5. Dow Corning 670 and 680 Fluids have a general formula of $R_nSiO_{(4-n)/2}$ wherein R is independently chosen from a hydrogen atom and a monovalent hydrocarbon group comprising 3 carbon atoms, wherein more than 80 mole % of R are propyl groups, n is a value from 1.0 to 1.4, more than 60 mole % of the copolymer comprises $RSiO_{3/2}$ units, and having a hydroxyl or alkoxy content from 0.2 to 10% by weight, for example between 1 and 4% by weight, preferably between 5 and 10% by weight, and more preferably between 6 and 8% by weight. Preferably, the polypropylsilsesquioxane resin has a molecular weight from about 5000 to about 30,000 and a Tg from about −5° C. to about 5° C.

Examples of commercially available polyphenylsilsesquioxane resins that may be mentioned include those sold:

by the company Dow Corning under the reference Dow Corning 217 Flake Resin, which is a polyphenylsilsesquioxane with silanol end groups; and by the company Wacker under the reference Belsil SPR 45 VP.

Silicone Acrylate Copolymer Film Former

Suitable silicone acrylate copolymer film formers include polymers comprising a siloxane group and a hydrocarbon group. For example, suitable polymers include polymers comprising a hydrocarbon backbone such as, for example, a backbone chosen from vinyl polymers, methacrylic polymers, and/or acrylic polymers and at least one chain chosen from pendant siloxane groups, and polymers comprising a backbone of siloxane groups and at least one pendant hydrocarbon chain such as, for example, a pendant vinyl, methacrylic and/or acrylic groups.

The silicone acrylate copolymer film former can be chosen from silicone/(meth)acrylate copolymers, such as those as described in U.S. Pat. Nos. 5,061,481, 5,219,560, and 5,262,087, and U.S. patent application 2012/0301415, the entire contents of all of which are hereby incorporated by reference.

The silicone acrylate copolymer film former may be selected from polymers derived from non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the products sold under the tradenames KP-545 (cyclopentasiloxane (and) acrylates/dimethicone copolymer), KP-543 (butyl acetate (and) acrylates/dimethicone copolymer), KP-549 (methyl trimethicone (and) acrylates/dimethicone copolymer), KP-550 (INCI name: isododecane (and) acrylate/dimethicone copolymer), and mixtures thereof. Additional examples include the acrylate/dimethicone copolymers sold by Dow Corning under the tradenames FA 4001 CM SILICONE ACRYLATE (cyclopentasiloxane (and) acrylates/polytrimethylsiloxymethacrylate copolymer) and FA 4002 ID SILICONE ACRYLATE (isododecane (and) acrylates/polytrimethylsiloxymethacrylate Copolymer), and mixtures thereof.

Further non-limiting examples of such polymers and their synthesis are disclosed, for example, in U.S. Pat. Nos. 4,972,037, 5,061,481, 5,209,924, 5,849,275, and 6,033,650, and PCT applications WO 93/23446, WO 95/06078 and WO 01/32737, the disclosures of all of which are hereby incorporated by reference. These polymers may be sourced from various companies. One such company is Minnesota Mining and Manufacturing Company which offers these types of polymers under the tradenames "Silicone Plus" polymers (for example, poly(isobutyl methacrylate-co-methyl FOSEA)-g-poly(dimethylsiloxane), sold under the tradename SA 70-5 IBMMF).

Other non-limiting examples of useful silicone acrylate copolymer film formers include silicone/acrylate graft terpolymers, for example, the copolymers described in PCT application WO 01/32727, the disclosure of which is hereby incorporated by reference.

Other useful polymers include those described in U.S. Pat. No. 5,468,477, the disclosure of which is hereby incorporated by reference. A non-limiting example of these polymers is poly(dimethylsiloxane)-g-poly(isobutyl methacrylate), which is commercially available from 3M Company under the tradename VS 70 IBM.

Suitable silicone acrylate copolymer film formers include silicone/(meth)acrylate copolymers, such as those as described in U.S. Pat. Nos. 5,061,481, 5,219,560, and 5,262,087, the disclosures of which are hereby incorporated by reference. Still further non-limiting examples of such silicone film formers are non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the product sold under the tradename KP-545, or KP550

Other non-limiting examples of silicone acrylate copolymer film formers suitable for use in the present invention are silicone esters comprising units of formulae (A) and (B), disclosed in U.S. Pat. Nos. 6,045,782, 5,334,737, and 4,725,658, the disclosures of which are hereby incorporated by reference:

  (A); and

  (B)

wherein

R and R', which may be identical or different, are each chosen from optionally substituted hydrocarbon groups;

a and b, which may be identical or different, are each a number ranging from 0 to 3, with the proviso that the sum of a and b is a number ranging from 1 to 3, x and y, which may be identical or different, are each a number ranging from 0 to 3, with the proviso that the sum of x and y is a number ranging from 1 to 3;

$R^E$, which may be identical or different, are each chosen from groups comprising at least one carboxylic ester.

According to preferred embodiments, $R^E$ groups are chosen from groups comprising at least one ester group formed from the reaction of at least one acid and at least one alcohol.

According to preferred embodiments, the at least one acid comprises at least two carbon atoms. According to preferred embodiments, the at least one alcohol comprises at least ten carbon atoms. Non-limiting examples of the at least one acid include branched acids such as isostearic acid, and linear acids such as behenic acid. Non-limiting examples of the at least one alcohol include monohydric alcohols and polyhydric alcohols, such as n-propanol and branched etheralkanols such as (3,3,3-trimethylolpropoxy)propane.

Further non-limiting examples of the at least one silicone acrylate copolymer film former include liquid siloxy silicates and silicone esters such as those disclosed in U.S. Pat. No. 5,334,737, the disclosure of which is hereby incorporated by reference, such as diisostearoyl trimethylolpropane siloxysilicate and dilauroyl trimethylolpropane siloxy silicate, which are commercially available from General Electric under the tradenames SF 1318 and SF 1312, respectively.

Acrylic Polymer Film Formers

Acceptable acrylic polymer film forming agents are known in the art and include, but are not limited to, those disclosed in U.S. patent application 2004/0170586 and U.S. patent application 2011/0020263, the entire contents of which are hereby incorporated by reference in their entirety.

"Acrylic polymer film formers" as used herein refers to polymers that are film forming agents and which are based upon one or more (meth)acrylic acid (and corresponding (meth)acrylate) monomers or similar monomers but which do not contain a silicone or siloxane group.

Non-limiting representative examples of such film forming agents include copolymers containing at least one apolar monomer, at least one olefinically unsaturated monomer, and at least one vinylically functionalized monomer.

For the apolar monomers, acrylic monomers which comprise acrylic and methacrylic esters with alkyl groups composed of 4 to 14 C atoms, preferably 4 to 9 C atoms are preferred. Examples of monomers of this kind are n-butyl acrylate, n-butyl methacrylate, n-pentyl acrylate, n-pentyl methacrylate, n-amyl acrylate, n-hexyl acrylate, hexyl methacrylate, n-heptyl acrylate, n-octyl acrylate, n-octyl methacrylate, n-nonyl acrylate, isobutyl acrylate, isooctyl acrylate, isooctyl methacrylate, and their branched isomers, such as, for example, 2-ethylhexyl acrylate, 2-ethylhexyl methacrylate.

For olefinically unsaturated monomers, it is preferred to use monomers having functional groups selected from hydroxyl, carboxyl, sulphonic acid groups, phosphonic acid groups, acid anhydrides, epoxides, and amines. Particularly preferred examples of olefinically unsaturated monomers include acrylic acid, methacrylic acid, itaconic acid, maleic acid, fumaric acid, crotonic acid, aconitic acid, dimethylacrylic acid, beta-acryloyloxypropionic acid, trichloracrylic acid, vinylacetic acid, vinylphosphonic acid, itaconic acid, maleic anhydride, hydroxyethyl acrylate, hydroxypropyl acrylate, hydroxyethyl methacrylate, hydroxypropyl methacrylate, 6-hydroxyhexyl methacrylate, allyl alcohol, glycidyl acrylate, glycidyl methacrylate.

For vinylically functionalized compounds, preferred monomers include monomers which are copolymerizable with one or both of the previously discussed monomers and include, for example, methyl acrylate, ethyl acrylate, propyl acrylate, methyl methacrylate, ethyl methacrylate, benzyl acrylate, benzyl methacrylate, sec-butyl acrylate, tert-butyl acrylate, phenyl acrylate, phenyl methacrylate, isobornyl acrylate, isobornyl methacrylate, tert-butylphenyl acrylate, tert-butylphenyl methacrylate, dodecyl methacrylate, isodecyl acrylate, lauryl acrylate, n-undecyl acrylate, stearyl acrylate, tridecyl acrylate, behenyl acrylate, cyclohexyl methacrylate, cyclopentyl methacrylate, phenoxyethyl acrylate, phenoxyethyl methacrylate, 2-butoxyethyl methacrylate, 2-butoxyethyl acrylate, 3,3,5-trimethylcyclohexyl acrylate, 3,5-dimethyladamantyl acrylate, 4-cumylphenyl methacrylate, cyanoethyl acrylate, cyanoethyl methacrylate, 4-biphenyl acrylate, 4-biphenyl methacrylate, 2-naphthyl acrylate, 2-naphthyl methacrylate, tetrahydrofurfuryl acrylate, diethylaminoethyl acrylate, diethylaminoethyl methacrylate, dimethylaminoethyl acrylate, dimethylaminoethyl methacrylate, 2-butoxyethyl acrylate, 2-butoxyethyl methacrylate, methyl 3-m ethoxyacrylate, 3-methoxybutyl acrylate, phenoxyethyl acrylate, phenoxyethyl methacrylate, 2-phenoxyethyl methacrylate, butyldiglycol methacrylate, ethylene glycol acrylate, ethylene glycol monomethylacrylate, methoxy-polyethylene glycol methacrylate 350, methoxy-polyethylene glycol methacrylate 500, propylene glycol monomethacrylate, butoxydiethylene glycol methacrylate, ethoxytriethylene glycol methacrylate, dimethylaminopropylacrylamide, dimethylaminopropylmethacrylamide, N-(1-methylundecyl)acrylamide, N-(n-butoxymethyl)acrylamide, N-(butoxymethyl) methacrylamide, N-(ethoxymethyl)acrylamide, N-(n-octadecyl)acrylamide, and also N,N-dialkyl-substituted amides, such as, for example, N,N-dimethylacrylamide, N,N-dimethylmethacrylamide, N-benzylacrylamides, N-isopropylacrylamide, N-tert-butylacrylamide, N-tert-octylacrylamide, N-methylolacrylamide, N-methylolmethacrylamide, acrylonitrile, methacrylonitrile, vinyl ethers, such as vinyl methyl ether, ethyl vinyl ether, vinyl isobutyl ether, vinyl esters, such as vinyl acetate, vinyl chloride, vinyl halides, vinylidene chloride, vinylidene halide, vinylpyridine, 4-vinylpyridine, N-vinylphthalimide, N-vinyllactam, N-vinylpyrrolidone, styrene, a- and p-methylstyrene, a-butylstyrene, 4-n-butylstyrene, 4-n-decylstyrene, 3,4-dimethoxystyrene, macromonomers such as 2-polystyrene-ethyl methacrylate (molecular weight Mw of 4000 to 13 000 g/mol), poly(methyl methacrylate)ethyl methacrylate (Mw of 2000 to 8000 g/mol).

An example of an acrylic polymer film former is a copolymer of acrylic acid, isobutyl acrylate and isobornyl acetate such as that sold under the names Pseudoblock (Chimex) and Synamer-3. In both of these commercial products, the copolymer is present with a solvent in a 1:1 ratio (50% solid). Another preferred film former is Poly (isobornyl methacrylate-co-isobornyl acrylate-co-isobutyl acrylate-co-acrylic acid) at 50% of active material in 50% of octyldodecyl neopentanoate, (Mexomere PAZ from Chimex).

Vinylpyrrolidone Polymer Film Formers

Acceptable vinylpyrrolidone homopolymer or copolymer film formers include, for example, crosslinked or non-crosslinked vinylpyrrolidone homopolymers such as the Polymer ACP-10, as well as copolymers produced from alpha-olefin and vinylpyrrolidone in which, preferably, the copolymer contains vinylpyrrolidone and an alkyl component containing at least one C4-C30 moiety in a concentration preferably from 10 to 80 percent such as those available from Ashland under the Ganex name such as, for example, VP/eicosene (GANEX V-220) and VP/tricontanyl copolymer (GANEX WP660).

According to preferred embodiments of the present invention, Component A comprises at least one silicone acrylate copolymer film former.

According to preferred embodiments of the present invention, Component A comprises at least one silicone resin film former. Preferably, the at least one silicone resin film former is a polypropylsilsesquioxane resin.

According to preferred embodiments of the present invention, Component A comprises at least one silicone acrylate copolymer film former and at least one silicone resin film former. Preferably, the at least one silicone resin film former is a polypropylsilsesquioxane resin.

According to preferred embodiments, the film forming agent(s) (active material) is/are preferably present in an amount of from about 0.01% to about 90% by weight, preferably from 0.08% to 80% by weight, and preferably from 0.1% to 60% by weight of the total weight of Component A, including all ranges and subranges therebetween.

According to preferred embodiments, the weight ratio of film forming agent(s) in Component A to silicone compound (s) in Component B is from 1:75 to 20:1, preferably from 1:50 to 10:1, and preferably from 1:20 to 10:1, including all ranges and subranges therebetween.

Shine (Gloss) Enhancing Agents

According to preferred embodiments of the present invention, Component B comprises at least one shine enhancing agent. Preferably, the shine (gloss) enhancing agent is selected from the group consisting of agents which facilitate self-leveling of a Layer, agents which have a high refractive index, or mixtures thereof.

Suitable shine enhancing agents include those compounds having a refractive index ranging from about 1.45 to about 1.60, and a weight average molecular weight of less than 15,000, preferably less than 10,000, and preferably less than 2,000. Examples of such agents include, but are not limited to, phenylated silicones such as those commercialized under the trade name "ABIL AV 8853" by Goldschmidt, those commercialized under the trade names "DC 554", "DC 555", "DC 556" and "SF 558" by Dow Corning, and those commercialized under the trade name "SILBIONE 70633 V 30" by Rhone-Poulenc.

Additional examples of suitable phenylated silicones include, but are not limited to, those commercialized by Wacker Silicones such as BELSIL PDM 20, a phenylated silicone with a viscosity at 25° C. of approximately 20 cSt; BELSIL PDM 200, a phenylated silicone with a viscosity at 25° C. of approximately 200 cSt; BELSIL PDM 1000, a phenylated silicone with a viscosity at 25° C. of approximately 1000 cSt.

For example, suitable phenylated silicone oils include, but are not limited to, trimethylsiloxyphenyl dimethicone, trimethyl pentaphenyl trisiloxane, diphenylsiloxy phenyl trimethicone, and mixtures thereof.

Additional examples of suitable shine enhancing agents include, but are not limited to, polycyclopentadiene, poly (propylene glycol) dibenzoate (nD=1.5345), aminopropyl phenyl trimethicone (nD=1.49-1.51), pentaerythrityl tetraoleate commercially available as PURESYN 4E68 (nD=1.473) from ExxonMobil, and PPG-3 benzyl ether myristate commercially available as CRODAMOL STS (nD=1.4696) from Croda Inc.

Particularly preferred shine enhancing agents are the phenylated silicones such as phenyl trimethicone, and trimethyl pentaphenyl trisiloxane, and esters such as pentaerythrityl tetraoleate, and PPG-3 benzyl ether myristate.

Suitable shine enhancing agents include those which provide self-leveling properties to the compositions of the present invention. Suitable examples of such compositions include, but are not limited to, the silicone compounds discussed below.

The silicone compound can be a silicone gum corresponding to the formula:

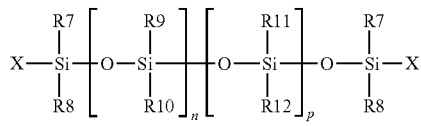

in which:

$R_7$, $R_8$, $R_{11}$ and $R_{12}$ are identical or different, and each is chosen from alkyl radicals comprising from 1 to 6 carbon atoms, $R_9$ and $R_{10}$ are identical or different, and each is chosen from alkyl radicals comprising from 1 to 6 carbon atoms and aryl radicals, X is chosen from alkyl radicals comprising from 1 to 6 carbon atoms, a hydroxyl radical and a vinyl radical, n and p are chosen so as to give the silicone gum a viscosity of from 350 cSt to 50,000,000 cSt, preferably from 500 cSt to 40,000,000 cSt, preferably from 750 cSt to 30,000,000 cSt, preferably from 850 cSt to 20,000,000 cSt, preferably from 950 cSt to 18,000,000 cSt and preferably from 1000 cSt to 10,000,000 cSt, including all ranges and subranges therebetween. A particularly preferred range is from 20,000 cSt to 800,000 cSt, with 25,000 cSt to 750,000 cSt being most preferred.

In general, n and p can each take values ranging from 0 to 10,000, such as from 0 to 5,000.

Among the silicone gums which can be used according to the invention, mention may be made of those for which:

the substituents $R_7$ to $R_{12}$ and X represent a methyl group, p=0 and n=2 700, such as the product sold or made under the name SE30 by the company General Electric, the substituents $R_7$ to $R_{12}$ and X represent a methyl group, p=0 and n=2 300, such as the product sold or made under the name AK 500 000 by the company Wacker, the substituents $R_7$ to $R_{12}$ represent a methyl group, the substituent X represents a hydroxyl group, p=0 and n=2 700, as a 13% solution in cyclopentasiloxane, such as the product sold or made under the name Q2-1401 by the company Dow Corning, the substituents $R_7$ to $R_{12}$ represent a methyl group, the substituent X represents a hydroxyl group, p=0 and n=2 700, as a 13% solution in polydimethylsiloxane, such as the product sold or made under the name Q2-1403 by the company Dow Corning, and the substituents $R_7$, $R_8$, $R_{11}$, $R_{12}$ and X represent a methyl group and the substituents $R_9$ and $R_{10}$ represent an aryl group, such that the molecular weight of the gum is about 600 000, for instance the product sold or made under the name 761 by the company Rhône-Poulenc (Rhodia Chimie).

In preferred embodiments, the silicone gum correspond to the following formula:

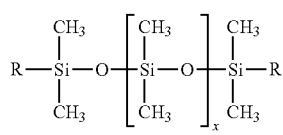

In this formula the terminal Si's can also be other than methyl and may be represented with substitutions on the repeating Si such that the R group is an alkyl of 1 to 6 carbon atoms, which may be linear, branched and/or functionalized selected from methyl, ethyl, propyl, isopropyl, butyl, isobutyl, t-butyl, amyl, hexyl, vinyl, allyl, cycohexyl, phenyl, and mixtures thereof. The silicone gums employed in the present invention may be terminated by triorganosilyl groups of the formula $R'_3$ where R' is a radical of monovalent hydrocarbons containing from 1 to 6 carbon atoms, hydroxyl groups, alkoxyl groups and mixtures thereof.

According to preferred embodiments, Component B/Layer B has a self-leveling property which results in a flatter interface between Layer A and Layer B and/or between Layer B and air, and this flatter interface results in light diffraction, refraction and/or reflection properties for Layer B which enhances the shine of the composition.

According to preferred embodiments of the present invention, at least one silicone compound such as a silicone fluid (for example, phenylated silicones described above) and/or silicone gum is present in the compositions of the present invention.

According to preferred embodiments of the present invention, at least two silicone compounds such as silicone fluids (for example, phenylated silicones described above) and/or silicone gums are present in the compositions of the present invention.

According to preferred embodiments of the present invention, Component B comprises one or more silicone compound(s) in amounts sufficient to achieve a viscosity of 30,000 cSt to 900,000 cSt, preferably 40,000 cSt to 800,000 cSt, and preferably 60,000 cSt to 750,000 cSt, including all ranges and subranges therebetween such as, for example, 60,000 cSt to 900,000 cSt. By way of non-limiting example, a dimethiconol of viscosity between 2.5 million cSt and 7.5 million cSt (for example, 5 million cSt) can be combined with a dimethicone of viscosity between 500,000 cSt and 2 million cSt (for example, 1 million cSt) and a dimethicone of viscosity of 1000 cSt in amounts to achieve the desired viscosity of the combined materials.

According to preferred embodiments, if present, agent(s) which facilitate self-leveling of a Layer such as silicone gum(s) is/are preferably present in an amount of from about 0.01% to about 90% by weight, preferably from 1% to 85% by weight, and preferably from 5% to 80% by weight of the total weight of the composition, including all ranges and subranges therebetween.

According to preferred embodiments, if present, agent(s) which have a high refractive index such as phenylated silicone oil(s) is/are preferably present in an amount of from about 0.05% to about 90% by weight, preferably from 0.1% to 50% by weight, and preferably from 1% to 40% by weight of the total weight of the composition, including all ranges and subranges therebetween.

Matte Enhancing Agents (Mattifying Agent)

According to embodiments of the present invention, Component B comprises at least one matte enhancing agent. With respect to Component B, the at least one matte enhancing agent can be added regardless of whether Component B is not self-leveling and/or Layer B has refractive properties to impart matte properties to the composition as described above.

Suitable matte enhancing agents include, but are not limited to, mattifying fillers such as, for example, talc, silica, silicone elastomers, and polyamides, and hydrocarbon waxes such as, for example, beeswax and copernicia cerifera (carnauba) wax.

According to preferred embodiments, the matte enhancing (s) is/are preferably present in an amount of from about 0.05% to about 90% by weight, preferably from 0.1% to 50% by weight, and preferably from 1% to 35% by weight of the total weight of the composition, including all ranges and subranges therebetween.

Coloring Agents

According to preferred embodiments of the present invention, compositions further comprising at least one coloring agent are provided.

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, ß-carotene, soybean oil, Sudan Brown, DC Yellow 11, DC Violet 2, DC Orange 5, annatto, and quinoline yellow.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum. If present, it is preferred that the amount of coloring agent present in the composition is less than about 50%, preferably less than 40%, preferably less than 30%, preferably less than 20%, preferably less than 10%, preferably 5% or less by weight of the total weight of the composition, including all ranges and subranges therebetween such as, for example, 1% to 20%.

Oil Phase

According to preferred embodiments of the present invention, compositions further comprising at least one fatty substance are provided. Suitable fatty substances include oil(s) and/or hydrocarbon wax(es). "Oil" means any non-aqueous medium which is liquid at ambient temperature (25° C.) and atmospheric pressure (760 mm Hg). A hydrocarbon "wax" for the purposes of the present disclosure is a lipophilic fatty compound that is solid at ambient temperature (25° C.) and changes from the solid to the liquid state reversibly, having a melting temperature of more than 30° C. and, for example, more than 45° C., which can be as high as 150° C., a hardness of more than 0.5 MPa at ambient temperature, and an anisotropic crystalline organization in the solid state. By taking the hydrocarbon wax (and/or the silicone wax component discussed above) to its melting temperature, it is possible to use wax(es) by themselves as carriers and/or it is possible to make wax(es) miscible with the oils to form a microscopically homogeneous mixture.

Suitable oils include volatile and/or non-volatile oils. Such oils can be any acceptable oil including but not limited to silicone oils and/or hydrocarbon oils.

According to certain embodiments, the compositions of the present invention preferably comprise one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to certain embodiments of the present invention, the composition of preferably comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isohexacecane, isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

According to certain embodiments of the present invention, the composition comprises at least one non-volatile oil. Examples of non-volatile oils that may be used in the present invention include, but are not limited to, polar oils such as:

- hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;
- synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, octyldodecyl neopentanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;
- synthetic ethers containing from 10 to 40 carbon atoms;
- $C_8$ to $C_{26}$ fatty alcohols, for instance oleyl alcohol, cetyl alcohol, stearyl alcohol, and cetearly alcohol; and
- mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

According to preferred embodiments, if present, the at least one oil is present in the compositions of the present invention in an amount ranging from about 1 to about 80% by weight, more preferably from about 5 to about 70% by weight, and most preferably from about 10 to about 60% by weight, based on the total weight of the composition, including all ranges and subranges within these ranges.

According to preferred embodiments of the present invention, the compositions of the present invention further comprise at least one hydrocarbon wax. Suitable examples of waxes that can be used in accordance with the present disclosure include those generally used in the cosmetics field: they include those of natural origin, such as beeswax, carnauba wax, candelilla wax, ouricoury wax, Japan wax, cork fibre wax or sugar cane wax, rice wax, montan wax, paraffin wax, lignite wax or microcrystalline wax, ceresin or ozokerite, and hydrogenated oils such as hydrogenated castor oil or jojoba oil; synthetic waxes such as the polyethylene waxes obtained from the polymerization or copolymerization of ethylene, and Fischer-Tropsch waxes, or else esters of fatty acids, such as octacosanyl stearate, glycerides which are concrete at 30° C., for example at 45° C.

According to preferred embodiments of the present invention, the compositions of the present invention further include at least one long-chain alcohol wax. Preferably, the at least one long-chain alcohol wax has an average carbon chain length of between about 20 and about 60 carbon atoms, most preferably between about 30 and about 50 carbon atoms. Suitable examples of long-chain alcohol waxes include but are not limited to alcohol waxes commercially available from Baker Hughes under the Performacol trade name such as, for example, Performacol 350, 425 and 550. Most preferably, the long-chain alcohol wax has a melting temperature range from about 93° C. to about 105° C.

According to preferred embodiments, the compositions of the present invention contain less than 1% hydrocarbon wax.

According to preferred embodiments, the compositions of the present invention contain less than 0.5% hydrocarbon wax.

According to preferred embodiments, the compositions of the present invention contain no hydrocarbon wax.

If present, the hydrocarbon wax or waxes may be present in an amount ranging from 1 to 30% by weight relative to the total weight of the composition, for example from 2 to 20%, and for example from 3 to 10%, including all ranges and subranges therebetween.

Aqueous Phase

The compositions of the present invention may also contain water. When present, water is preferably present in an amount of from about 10% to about 80% by weight, preferably from about 20% to about 70% by weight, preferably from about 35% to about 65% by weight, including all ranges and subranges therebetween, all weights being based on the total weight of the composition.

Additional Additives

The composition of the invention can also comprise any additive usually used in the field under consideration. For example, dispersants such as poly(12-hydroxystearic acid), antioxidants, essential oils, sunscreens, preserving agents, fragrances, fillers, neutralizing agents, cosmetic and dermatological active agents such as, for example, emollients, moisturizers, vitamins, essential fatty acids, surfactants, silicone elastomers, thickening agents, gelling agents, particles, pasty compounds, viscosity increasing agents can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* (9$^{th}$ ed. 2002).

According to preferred embodiments, the compositions of the present invention do not contain surfactants.

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%)

relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the eyelashes of human beings.

In particular, suitable gelling agents for the oil phase include, but are not limited to, lipophilic or hydrophilic clays.

The term "hydrophilic clay" means a clay that is capable of swelling in water; this clay swells in water and forms after hydration a colloidal dispersion. These clays are products that are already well known per se, which are described, for example, in the book "Mineralogie des argiles", S. Caillere, S. Henin, M. Rautureau, $2^{nd}$ edition 1982, Masson, the teaching of which is included herein by way of reference. Clays are silicates containing a cation that may be chosen from calcium, magnesium, aluminium, sodium, potassium and lithium cations, and mixtures thereof. Examples of such products that may be mentioned include clays of the smectite family such as montmorillonites, hectorites, bentonites, beidellites and saponites, and also of the family of vermiculites, stevensite and chlorites. These clays may be of natural or synthetic origin.

Hydrophilic clays that may be mentioned include smectite products such as saponites, hectorites, montmorillonites, bentonites and beidellite. Hydrophilic clays that may be mentioned include synthetic hectorites (also known as laponites), for instance the products sold by the company Laporte under the names Laponite XLG, Laponite RD and Laponite RDS (these products are sodium magnesium silicates and in particular sodium lithium magnesium silicates); bentonites, for instance the product sold under the name Bentone HC by the company Rheox; magnesium aluminium silicates, especially hydrated, for instance the products sold by the Vanderbilt Company under the names Veegum Ultra, Veegum HS and Veegum DGT, or calcium silicates, and especially the product in synthetic form sold by the company under the name Micro-cel C.

The term "lipophilic clay" means a clay that is capable of swelling in a lipophilic medium; this clay swells in the medium and thus forms a colloidal dispersion. Examples of lipophilic clays that may be mentioned include modified clays such as modified magnesium silicate (Bentone Gel VS38 from Rheox), and hectorites modified with a $C_{10}$ to $C_{22}$ fatty-acid ammonium chloride, for instance hectorite modified with distearyldimethylammonium chloride (CTFA name: disteardimonium hectorite) sold under the name Bentone 38 CE by the company Rheox or Bentone 38V® by the company Elementis.

In particular, among the gelling agents that may be used, mention may be made of silica particles. Preferably, the silica particles are fumed silica particles.

Suitable silicas include, but are not limited to, hydrophobic silicas, such as pyrogenic silica optionally with hydrophobic surface treatment whose particle size is less than 1 micron, preferably less than 500 nm, preferably less than 100 nm, preferably from 5 nm to 30 nm, including all ranges and subranges therebetween. It is in fact possible to modify the surface of silica chemically, by a chemical reaction producing a decrease in the number of silanol groups present on the surface of the silica. The silanol groups can notably be replaced with hydrophobic groups: a hydrophobic silica is then obtained. The hydrophobic groups can be:

trimethylsiloxyl groups, which are notably obtained by treatment of pyrogenic silica in the presence of hexamethyldisilazane. Silicas treated in this way are called "Silica silylate" according to the CTFA (6th edition, 1995). They are for example marketed under the references "AEROSIL R812®" by the company Degussa, "CAB-O-SIL TS-530®" by the company Cabot;

dimethylsilyloxyl or polydimethylsiloxane groups, which are notably obtained by treatment of pyrogenic silica in the presence of polydimethylsiloxane or dimethyldichlorosilane. Silicas treated in this way are called "Silica dimethyl silylate" according to the CTFA (6th edition, 1995). They are for example marketed under the references "AEROSIL R972®", "AEROSIL R974®" by the company Degussa, "CAB-O-SIL TS-610®", "CAB-O-SIL TS-720®" by the company Cabot.

Preferably, the gelling agent, if present, is present in the lip composition of the present invention in amounts of active material generally ranging from about 0.1% to about 10%, preferably from about 0.25% to about 5%, and more preferably from about 0.5% to about 3.5%, by weight, based on the total weight of the lip gloss composition, including all ranges and subranges in between.

According to the present invention, the compositions of the present invention are lip gloss compositions for application to lips. In accordance with these embodiments, the compositions of the present invention can contain ingredients typically found in lip gloss compositions such as, for example, coloring agents, waxes, and gelling agents. Further, the compositions can contain water or be anhydrous. Also, the compositions can be solid or non-solid.

According to preferred embodiments of the present invention, methods of treating, caring for and/or making up lips by applying compositions of the present invention to the lips in an amount sufficient to treat, care for and/or make up the lips are provided.

According to yet other preferred embodiments, methods of enhancing the appearance of lips by applying compositions of the present invention to the lips in an amount sufficient to enhance the appearance of the lips are provided.

According to preferred embodiments of the present invention, methods of applying compositions of the present invention lips comprising mixing or blending the composition so that the non-homogeneous components are temporarily substantially homogeneous, and applying the composition comprising the temporarily substantially homogeneous components to the lips are provided. Subsequent to application to the lips, the components separate to form a multilayer structure on the lips.

According to preferred embodiments of the present invention, kits comprising (1) at least one container; (2) at least one applicator; and (3) at least one lip gloss composition capable of forming a multilayer structure after application to a lip, wherein the composition comprises at least two components as described above prior to application.

In accordance with the preceding preferred embodiments, the compositions of the present invention are applied topically to the desired area of the lips in an amount sufficient to treat, care for and/or make up the lips, to cover or hide defects associated with lips, skin imperfections or discolorations, or to enhance the appearance of lips. The compositions may be applied to the desired area as needed, preferably once daily, and then preferably allowed to dry before subjecting to contact such as with clothing or other objects. Preferably, the composition is allowed to dry for about 4 minutes or less, more preferably for about 2 minutes or less.

Also in accordance with the preceding preferred embodiments, compositions are preferably contained in a suitable container for lip gloss compositions. Suitable shapes of such containers include, but are not limited to, any geometric shape such as, for example, square, rectangular, pyramidal, oval, circular, hemispherical, etc. Further, the container may be made of flexible or inflexible material.

Similarly, any applicator suitable for application of lip gloss compositions can be used in accordance with the present invention, with suitable examples of types of applicators including, but not limited to, a brush, stick, pad, roller ball, etc.

Preferably, either (1) the container is capable of mixing or blending the composition of the present invention so that the non-homogeneous components are temporarily substantially homogeneous; (2) the applicator is capable of mixing or blending the composition of the present invention so that the non-homogeneous components are temporarily substantially homogeneous; (3) the container and the applicator working together are capable of mixing or blending the composition of the present invention so that the non-homogeneous components are temporarily substantially homogeneousin accordance with the preceding preferred embodiments. For example, a flexible container by virtue of its flexibility could create sufficient forces when manipulated to temporarily mix or blend the composition of the present invention so that the non-homogeneous components are temporarily substantially homogeneous; an applicator by virtue of its design could create sufficient forces when withdrawn from the container to temporarily mix or blend the composition of the present invention so that the non-homogeneous components are temporarily substantially homogeneous; or (4) an inflexible container and an applicator by virtue of their synergistic design elements could create sufficient forces when the applicator is withdrawn from the container to temporarily mix or blend the composition of the present invention so that the non-homogeneous components are temporarily substantially homogeneous.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Example 1—Exemplary Lip Gloss Compositions

The following composition is an exemplary composition of the present invention which can be prepared by the identified method:

| Ingredient | Amount |
|---|---|
| Pigments | 1-15% |
| Silicon Resin Film Former | 5-45% |

-continued

| Ingredient | Amount |
|---|---|
| Silicone Acrylate Film Former | 8-35% |
| Semi-Crystalline Acrylate Copolymer | 1-20% |
| Silicone Wax | 1-20% |
| PDMS | 5-30% |
| Volatile Oils | 25-35% |
| Thickener | 0.1-2% |
| Shine Enhancing Agents | 0-15% |
| Preservative | 0-2% |

The compositions can be prepared using a high speed mixer. To a high speed mixer cup, all polymers can be added. The sample can then be mixed at 2500-3500 RPM until homogenous. The samples typically are opaque and not clear, and homogeneity can be deciphered by the sample smoothness. To the freshly mixed sample, pigments, pigments dispersions, and any other particles can be added in addition to the QS solvent. The sample can then be additionally mixed at 2500-3500 RPM until homogenous.

Example 2—Shine and Wear Properties

A base composition generally described in the following table was prepared and tested for shine and wear properties.

| Ingredient | Amount |
|---|---|
| Pigments | 1-15% |
| Silicon Resin Film Former | 5-45% |
| Silicone Acrvlate Film Former | 8-35% |
| PDMS | 5-30% |
| Volatile Oils | 5-30% |
| Fillers | 0-10% |
| Preservative | 0-2% |

This base composition was prepared and tested as a comparative composition (without further addition of ingredients, composition 1). To prepare a second composition (composition 2), to the same base composition 5% silicone wax was added. Also, to prepare a third composition (composition 3), 5% semi-crystalline acrylate copolymer was added. To prepare a fourth composition (composition 4), 2.2% silicone wax with additional silicone oil was added. To prepare a fifth composition (composition 4), 5% semi-crystalline acrylate copolymer was added into the fourth composition. All Five compositions had roughly the same wear properties, demonstrating that the semi-crystalline acrylate copolymer had little to no impact on wear properties when added to the above base composition.

However, it was noted for the base composition possessing good shine properties (composition 1), the addition of the semi-crystalline acrylate copolymer maintained the shine (composition 3 vs composition 1) For compositions having lesser/intermediate shine properties(for example, composition 4), however, it was noted that adding 5% semi-crystalline acrylate copolymer to the compositions was determined to significantly increase shine properties (Composition 5 vs composition 4).

Example 3—Slip (Lack of Friction) Properties

Similar base compositions to the composition in Example 2 were prepared. The compositions also contained 2.2% silicone wax. Using the base compositions, invention compositions were also prepared by adding 5% semi-crystalline acrylate copolymer. The coefficient of friction for the compositions was determined during application at around 10-15 (/s) of shear rate (this shear rate was selected as a representative shear rate of application to the skin). It was observed that friction was reduced by adding 5% semi-crystalline acrylate copolymer to the base composition compared to the base composition from example 2 containing no wax (Friction=0.45 vs. Friction=0.46) or with silicone wax which was actually higher than the base composition (Friction=0.47 vs. Friction=0.49). Accordingly, adding 5% semi-crystalline acrylate copolymer reduced friction (increased slip) upon application.

Example 4—Low Temperature Stability Testing

For low temperature stability testing, samples were cooled to a temperature of approximately 4 degrees Celsius and kept at this temperature for at least 1 month (in some cases, 2 months). The samples were then assessed for bulk solidification and application.

The Following compositions were tested for low temperature stability. Base composition with 5% silicone wax (composition 1) vs Base composition with 5% semi-crystalline acrylate copolymer (composition 2) vs Base composition with total 5% combination of silicone wax and semi-crystalline acrylate copolymer (composition 3). As demonstrated in the chart below, base compositions containing 5% silicone wax or 5% semi-crystalline acrylate copolymer alone solidified at low temperature and failed the stability criteria. However, compositions containing 5% semi-crystalline acrylate copolymer and silicone wax were stable and remained applicable.

| Sample | Low Temp Stability |
| --- | --- |
| Composition 1 containing 5% silicone wax | Failed (Solidified) |
| Composition 2 containing 5% semi-crystalline acrylate copolymer | Failed (Solidified) |
| Composition 3 (total silicone wax and semi-crystalline acrylate copolymer concentration at 5%) | Pass (Does not Solidify) |

What is claimed is:

1. A lip composition comprising at least one semi-crystalline acrylate copolymer, wherein the lip composition comprises Component A and Component B,
   wherein, prior to mixing the composition, Component A and Component B are non-homogeneous; wherein, immediately after mixing the composition, Component A and Component B are temporarily substantially homogeneous to form a mixed composition,
   wherein, after allowing the composition to rest at room temperature for 72 hours after mixing, Component A and Component B are non-homogeneous, and
   wherein the composition is capable of forming a multi-layer structure after application of the mixed composition to lips.

2. The lip composition of claim 1, wherein the lip composition is anhydrous.

3. The lip composition of claim 1, wherein the at least one semi-crystalline acrylate copolymer is acrylates/stearyl acrylate/dimethicone methacrylate copolymer and has at least one melting point of about 25° C. to about 35° C.

4. The lip composition of claim 1, wherein the composition further comprises a silicone wax component.

5. The lip composition of claim 4, wherein the silicone wax component has a melting point of about 25° C. to about 35° C.

6. The lip composition of claim 5, wherein the silicone wax component comprises at least one C12-C22 dimethicone.

7. The lip composition of claim 5, wherein the silicone wax component comprises at least one C16-C18 dimethicone.

8. The lip composition of claim 5, wherein the silicone wax component comprises bis stearyl dimethicone.

9. The lip composition of claim 8, wherein the at least one semi-crystalline acrylate copolymer is acrylates/stearyl acrylate/dimethicone methacrylate copolymer and has at least one melting point of about 25° C. to about 35° C.

10. The lip composition of claim 5, wherein the weight ratio of the at least one semi-crystalline acrylate copolymer to the silicone wax component ranges from about 10:1 to about 1:10.

11. The lip composition of claim 4, wherein the at least one semi-crystalline acrylate copolymer is acrylates/stearyl acrylate/dimethicone methacrylate copolymer and has at least one melting point of about 25° C. to about 35° C., the silicone wax component comprises bis stearyl dimethicone, the weight ratio of the at least one semi-crystalline acrylate copolymer to the silicone wax component ranges from about 4:1 to about 1:4, and the composition is anhydrous.

12. A method of applying the lip composition of claim 11 to lips comprising mixing the lip composition to form a mixed composition in which Component A and Component B are temporarily substantially homogeneous, and applying the mixed composition to lips.

13. A method of applying the lip composition of claim 1 to lips comprising mixing the lip composition to form a mixed composition in which Component A and Component B are temporarily substantially homogeneous, and applying the mixed composition to lips.

* * * * *